US011207035B2

United States Patent
Eibenberger et al.

(10) Patent No.: US 11,207,035 B2
(45) Date of Patent: Dec. 28, 2021

(54) SENSOR-BASED PATIENT TREATMENT SUPPORT

(71) Applicant: Siemens Healthcare GmbH, Erlangen (DE)

(72) Inventors: Eva Eibenberger, Nuremberg (DE); Ankur Kapoor, Plainsboro, NJ (US); Amitkumar Bhupendrakumar Shah, Fürth (DE); Vivek Singh, Princeton, NJ (US); Andreas Wimmer, Forchheim (DE); Philipp Hölzer, Baltimore, MD (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/815,040

(22) Filed: Mar. 11, 2020

(65) Prior Publication Data
US 2020/0323496 A1    Oct. 15, 2020

Related U.S. Application Data

(60) Provisional application No. 62/831,836, filed on Apr. 10, 2019.

(51) Int. Cl.
*A61B 5/00* (2006.01)
*G16H 70/20* (2018.01)
*G16H 40/63* (2018.01)
*G16H 30/40* (2018.01)
*G06T 1/00* (2006.01)
*G06T 11/00* (2006.01)
*G08B 3/10* (2006.01)
*A61B 6/04* (2006.01)
(Continued)

(52) U.S. Cl.
CPC ............ *A61B 5/746* (2013.01); *A61B 5/0035* (2013.01); *A61B 5/0077* (2013.01); *A61B 5/107* (2013.01); *A61B 5/1113* (2013.01); *A61B 5/6889* (2013.01); *A61B 5/6892* (2013.01); *A61B 6/0407* (2013.01); *A61B 6/102* (2013.01); *A61B 6/481* (2013.01); *A61B 8/40* (2013.01); *A61G 7/10* (2013.01); *G06T 1/0014* (2013.01); *G06T 11/005* (2013.01); *G08B 3/10* (2013.01); *G16H 30/40* (2018.01); *G16H 40/63* (2018.01); *G16H 50/30* (2018.01); *G16H 70/20* (2018.01); *A61G 2203/36* (2013.01); *A61G 2203/44* (2013.01); *G06T 2211/404* (2013.01)

(58) Field of Classification Search
CPC ..................................................... A61B 5/746
See application file for complete search history.

(56) References Cited

U.S. PATENT DOCUMENTS

| | | | |
|---|---|---|---|
| 2001/0025137 A1* | 9/2001 | Webb .................. | A61B 5/0031 600/300 |
| 2003/0125017 A1* | 7/2003 | Greene ................ | A61B 5/0002 455/414.1 |

(Continued)

*Primary Examiner* — Nabil H Syed
*Assistant Examiner* — Cal J Eustaquio

(57) ABSTRACT

A framework for sensor-based patient treatment support. In accordance with one aspect, one or more sensors are used to acquire sensor data of one or more objects of interest. The sensor data is then automatically interpreted to generate processing results. One or more actions may be triggered based on the processing results to support treatment of a patient, including supporting medical scanning of the patient.

20 Claims, 4 Drawing Sheets

(51) Int. Cl.
*A61G 7/10* (2006.01)
*A61B 5/107* (2006.01)
*A61B 5/11* (2006.01)
*A61B 8/00* (2006.01)
*A61B 6/00* (2006.01)
*A61B 6/10* (2006.01)
*G16H 50/30* (2018.01)

(56) References Cited

U.S. PATENT DOCUMENTS

| | | | |
|---|---|---|---|
| 2006/0174412 A1* | 8/2006 | Hornig | A61B 6/04 |
| | | | 5/600 |
| 2006/0285644 A1* | 12/2006 | Camus | A61B 6/102 |
| | | | 378/117 |
| 2016/0288568 A1* | 10/2016 | Brondum | B60B 33/026 |
| 2017/0311842 A1* | 11/2017 | Boettger | A61B 6/0407 |
| 2019/0297276 A1* | 9/2019 | Sachdev | A61B 1/00009 |
| 2020/0107884 A1* | 4/2020 | Razeto | G06T 7/33 |

* cited by examiner

SENSOR-BASED PATIENT TREATMENT SUPPORT

CROSS-REFERENCE TO RELATED APPLICATION

The present application claims the benefit of U.S. provisional application No. 62/831,836 filed Apr. 10, 2019, the entire contents of which are herein incorporated by reference.

TECHNICAL FIELD

The present disclosure generally relates to sensor data processing, and more particularly to sensor-based patient treatment support.

BACKGROUND

Trauma centers handle cases where there are life-threatening and critical traumatic injuries, such as falls, gunshot wounds or vehicle collisions. Highly-specialized surgeons work with the advanced equipment to increase the likelihood of survival in patients who are sent there. Operating Room (OR) staff work together to coordinate and navigate the patient through the phases of surgery to treat a wide variety of patients and issues in a timely manner.

The environment in the OR is intense and fast-paced. The treatment outcome of trauma patients is largely affected by when treatment can start. Such time criticality heightens requirements on speeding up prior diagnosis and transfer of the patient to and from diagnostic modalities. In the context of medical imaging, this may require timely transfer to the medical imaging modality (e.g., computed tomography or CT), speedy selection of appropriate acquisition parameters for the given injuries of the patient, easily operated medical scanning and an almost immediate diagnosis based on the medical images.

SUMMARY

Described herein is a framework for sensor-based patient treatment support. In accordance with one aspect, one or more sensors are used to acquire sensor data of one or more objects of interest. The sensor data is then automatically interpreted to generate processing results. One or more actions may be triggered based on the processing results to support treatment of a patient, including supporting medical scanning of the patient.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

Figure 1:
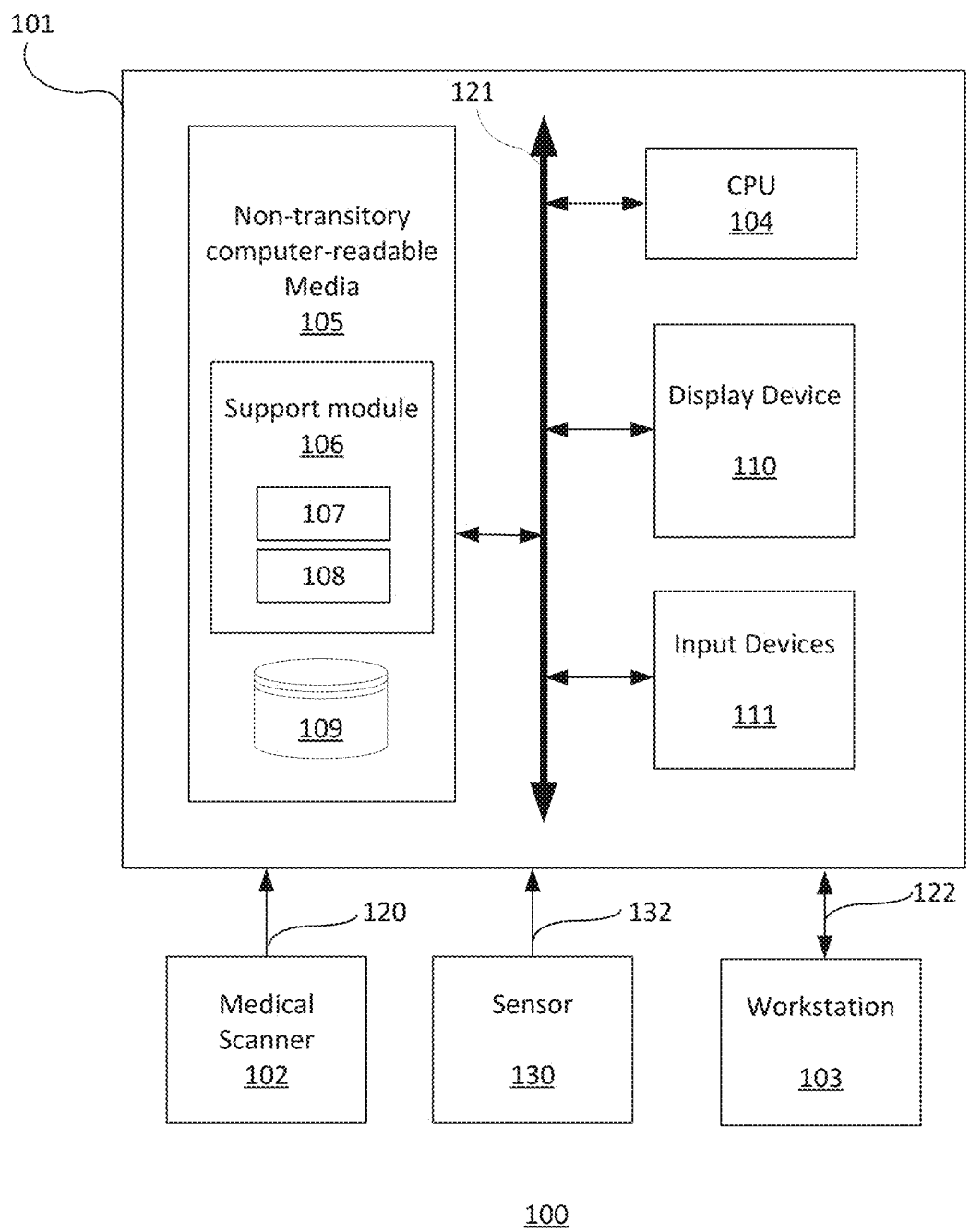
FIG. 1 is a block diagram illustrating an exemplary system.

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of an interventional or therapeutic procedure, which may include times when the radiation source is either on or off. From time to time, for convenience of description, CT imaging data (e.g., cone-beam CT imaging data) may be used herein as an exemplary imaging modality. It will be appreciated, however, that data from any type of imaging modality including but not limited to x-ray radiographs, MM, PET (positron emission tomography), PET-CT, SPECT, SPECT-CT, MR-PET, 3D ultrasound images or the like may also be used in various implementations.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

As used herein, the term "image" refers to multi-dimensional data composed of discrete image elements (e.g., pixels for 2D images and voxels for 3D images). The image may be, for example, a medical image of a subject collected by computer tomography, magnetic resonance imaging, ultrasound, or any other medical imaging system known to one skilled in the art. The image may also be provided from non-medical contexts, such as, for example, remote sensing systems, electron microscopy, etc. Although an image can be thought of as a function from $R^3$ to $R$, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

"Sensor data" as used herein refers to any data acquired by one or more sensors, such as monochromatic or color image data acquired by cameras. Sensor data may also include distance or range measurements provided by, for example, a structured light or time-of-flight sensor, a LIDAR sensor or an ultrasound sensor. Sensor data may be arranged in the shape of a matrix, wherein each element or pixel of the matrix represents a color, distance, range or depth value. Alternatively, sensor data may also be unstructured, such as in a cloud of surface points acquired by a LIDAR sensor.

The terms "pixels" for picture elements, conventionally used with respect to 2D imaging and image display, and "voxels" for volume image elements, often used with respect to 3D imaging, can be used interchangeably. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

Treatment of trauma patients requires a very thorough scan preparation and execution by the hospital/radiology team. To prepare for scanning, trauma patients must be carefully transferred from the transfer bed to the scan table to avoid, for example, additional injuries due to potential spine fractures. The height of the scan table may be manually adjusted to fit to the transfer bed.

Moreover, different scanner types or scan modes pose various constraints on the positioning of the patient on the scan table. For instance, the range on the table that can be scanned may be constrained. Specialized scan modes or protocols may impose further constraints, e.g. the range for which a flash spiral can be acquired or the dual energy CT field-of-view. If the patient or the body region to be examined is not placed within these limits, the acquired medical data may be incomplete. This may lead to the patient having to be repositioned on the table and the examination to be repeated, which is time-consuming and may entail additional radiation dose. The problem is that these kinds of constraints are not always clearly marked on the scan table. The team has to carefully ensure that the patient position is correct. However, due to blankets and/or external devices, relevant markers on the scan table may not be visible during patient transfer.

Additionally, devices (e.g., infusion device, blood transfusion device, lung ventilator) that are connected to the patient must also be carefully positioned, so that table and/or gantry movement during scanning will not cause collisions (e.g., pulling out of cables). The team needs to ensure that collision-free scanning is guaranteed. If during scanning, the team recognizes that a collision/pull-out may happen soon, it is either too late to react or the scan must be aborted immediately.

During scanning, the patient needs to be carefully supervised in order to identify critical patient conditions. For this purpose, sometimes 2D cameras are placed close to the gantry to allow the team to perform optical patient observation. Examinations may require the application of contrast agent to highlight vascular structures or organs. The team needs to determine the appropriate volume of contrast agent to administer to the patient. Lower contrast volume reduces the contrast load to the patient's organs. On the other hand, sufficient contrast volume is required to obtain good image quality. Weight-adapted contrast regimes are currently under investigation. These regimes require that the patient be placed on a scale before the scan. This, however, is not always possible for polytrauma and acute stroke patients. Today, even hemodynamically unstable patients are sometimes scanned with CT in order to identify, for example, the source of abdominal bleeding. In certain cases, automatic cardiac compression devices are used. However, the thoracic compression with those devices results in thoracic reconstructions with extreme motion artifacts. The scanning is often done in multiphase contrasts and for multiple body regions. Sometimes the patients' hands are also moved to different positions for ensuring good image quality. This examination can often take up to 10 minutes, which can cause further discomfort to the patient.

After scanning, the acquired medical data needs to be prepared for viewing and reading by the radiologist. In CT, tomographic images or slices are reconstructed from the acquired projection images. Therefore, the field-of-view for the reconstructed volume needs to be defined. Typically, a certain body region is covered in only one topogram or scout image (e.g., head/neck in a lateral topogram, chest/abdomen/pelvis in an anterior-posterior topogram). This allows the imaging system to automatically define the field-of-view of a reconstruction in two dimensions. However, the third dimension cannot be automatically identified precisely. Consequently, if the team uses automatic reconstructions, it can happen that due to skewed patient placement (not unlikely in trauma), the reconstructed image may not correctly represent the relevant anatomy (e.g., head is incompletely imaged on one side). To avoid this, manual reconstruction planning by a technologist is currently performed. However, such manual reconstruction planning is time-consuming.

Another challenge that may be encountered is that immediate interventions (e.g., a puncture of the lung in case of tension pneumothorax) are sometimes performed on the scan table. The surgical/interventional expert looks at the CT image data on a screen in order to quickly plan the therapy. The expert has to cognitively transfer the planning information from the display onto the patient to perform the intervention.

The present framework provides a sensor-based system and method that supports the treatment of patients. "Treatment" as used herein generally refers to medical scanning, diagnosis, intervention, assessment or any other action performed on the patient. In accordance with one aspect, the framework supports medical treatment of the patient, particularly medical scanning, by using sensor data. For example, it facilitates the transfer and positioning of the patient on the scan table for scanning or medical imaging (e.g., CT). As another example, the framework facilitates the appropriate selection of acquisition and reconstruction parameters for medical scanning. The framework may also provide additional parameters not directly related to the medical scan in order to augment patient assessment and diagnosis. These parameters may pertain to, for example, the detection of outer lesions, patient physiology or cognitive abilities.

The number of medical scans performed in, for example, the trauma operating room is increasing steadily. In addition, there is an increasing use of dedicated emergency department scanners. The present sensor-based framework facilitates a faster and safer workflow, better image quality, lower costs and more efficient patient assessment and diagnosis. These and other features and advantages will be described in more details herein.

FIG. 1 is a block diagram illustrating an exemplary system 100. The system 100 includes a computer system 101 for implementing the framework as described herein. In some implementations, computer system 101 operates as a standalone device. In other implementations, computer system 101 may be connected (e.g., using a network) to other machines, such as medical scanner 102, sensor 130 and workstation 103. In a networked deployment, computer system 101 may operate in the capacity of a server (e.g., thin-client server), a cloud computing platform, a client user machine in server-client user network environment, or as a peer machine in a peer-to-peer (or distributed) network environment.

In some implementations, computer system 101 comprises a processor or central processing unit (CPU) 104 coupled to one or more non-transitory computer-readable media 105 (e.g., computer storage or memory), a display device 110 (e.g., monitor) and various input devices 111 (e.g., mouse or keyboard) via an input-output interface 121. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 105. In particular, the present techniques may be implemented by a support module 106 that includes a processing module 107 and a control module 108.

Non-transitory computer-readable media 105 may include random access memory (RAM), read-only memory (ROM), magnetic floppy disk, flash memory, and other types of memories, or a combination thereof. The computer-readable program code is executed by CPU 104 to process data retrieved from, for example, medical scanner 102 and sensor 130. As such, the computer system 101 is a general-purpose computer system that becomes a specific purpose computer system when executing the computer-readable program code. The computer-readable program code is not intended to be limited to any particular programming language and implementation thereof. It will be appreciated that a variety of programming languages and coding thereof may be used to implement the teachings of the disclosure contained herein.

The same or different computer-readable media 105 may be used for storing a database (or dataset) 109. Such data may also be stored in external storage or other memories. The external storage may be implemented using a database management system (DBMS) managed by the CPU 104 and residing on a memory, such as a hard disk, RAM, or removable media. The external storage may be implemented on one or more additional computer systems. For example, the external storage may include a data warehouse system residing on a separate computer system, a cloud platform or system, a picture archiving and communication system (PACS), or any other hospital, medical institution, medical office, testing facility, pharmacy or other medical patient record storage system.

Medical scanner 102 is a radiological imaging modality that acquires medical image data 120 associated with at least one patient. Such medical image data 120 may be processed and stored in database 109. Medical scanner 102 may acquire medical image data 120 using techniques such as, but not limited to, high-resolution computed tomography (HRCT), magnetic resonance (MR) imaging, computed tomography (CT), helical CT, X-ray, angiography, positron emission tomography (PET), fluoroscopy, ultrasound, single photon emission computed tomography (SPECT), photoacoustics, microwaves, optical coherence tomography or a combination thereof.

One or more sensors 130 acquire sensor data 132. One or more sensors 130 may be, but is not limited to, an RGB (red, green, blue) camera, an infrared camera, a depth camera (e.g., time-of-flight sensor), a LIDAR sensor, a video camera, a plenoptic camera, a panoramic camera, a holographic camera, an ultrasound sensor, or a combination thereof. Sensor data 132 may be acquired by a single acquisition (e.g., a photo captured by a camera) or continuously in a stream (e.g., video captured by a camera or a stream of depth measurements acquired by a time-of-flight sensor). Sensor data 132 may include, but is not limited to, monochromatic images, color images, distance, depth or range data.

Workstation 103 may include a computer and appropriate peripherals, such as a keyboard and display device, and can be operated in conjunction with the entire system 100. For example, the workstation 103 may communicate directly or indirectly with the medical scanner 102 and/or sensor 130 so that the medical image data 120 and/or sensor data 132 can be displayed at the workstation 103. The workstation 103 may also provide other types of medical data 122 of a given patient. The workstation 103 may include a graphical user interface to receive user input via an input device (e.g., keyboard, mouse, touch screen, voice or video recognition interface, etc.) to input medical data 122.

It is to be further understood that, because some of the constituent system components and method steps depicted in the accompanying figures can be implemented in software, the actual connections between the systems components (or the process steps) may differ depending upon the manner in which the present framework is programmed. Given the teachings provided herein, one of ordinary skill in the related art will be able to contemplate these and similar implementations or configurations of the present framework.

Figure 2:
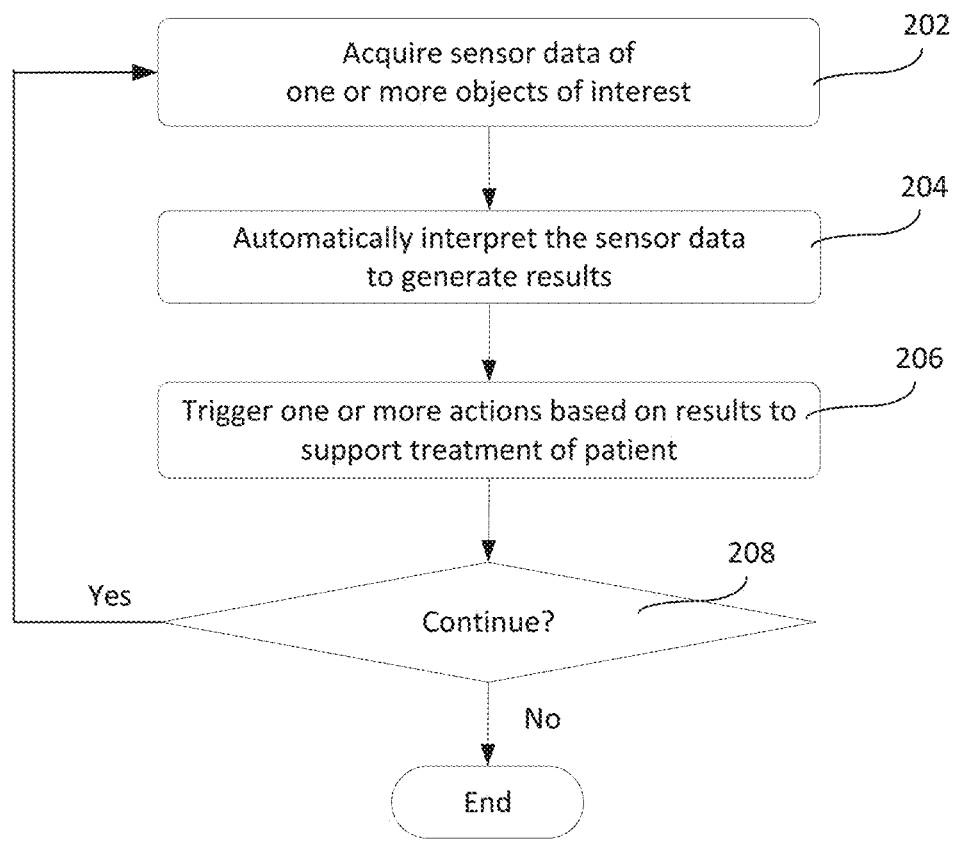
FIG. 2 shows an exemplary method of supporting treatment of a patient.

FIG. 2 shows an exemplary method 200 of supporting treatment of a patient. It should be understood that the steps of the method 200 may be performed in the order shown or a different order. Additional, different, or fewer steps may also be provided. Further, the method 200 may be implemented with the system 100 of FIG. 1, a different system, or a combination thereof.

At 202, one or more sensors 130 acquire sensor data 132 of one or more objects of interest. The objects of interest may be located in a medical scanning room or any other location where a medical scanner is used (e.g., operating room). The one or more objects of interest may be any object near the one or more sensors 130. Examples of objects of interest include, but are not limited to, at least a portion of the patient (e.g., body, face, chest), the patient transfer bed that is used to transport the patient into the operating room, the scan table that is used to hold the patient during medical imaging, medical equipment, medical staff, and/or a combination thereof. The one or more sensors 130 may be initiated to acquire sensor data when, for example, a patient is determined to be present in the room. The one or more sensors 130 may acquire the sensor data in a single acquisition, continuously or at predetermined time intervals.

The one or more sensors 130 may be a RGB (red, green, blue) camera, an infrared camera, a depth camera (e.g., time-of-flight sensor), a LIDAR sensor, a video camera, a plenoptic camera, a panoramic camera, a holographic camera, an ultrasound sensor, or a combination thereof. For example, the one or more sensors 130 may be a panoramic camera to allow capture of images with elongated fields of view covering, for example, both the patient and surrounding medical staff. Additionally, the one or more sensors 130 may be a plenoptic (or light field) camera to enable focusing of different planes.

Figure 3:
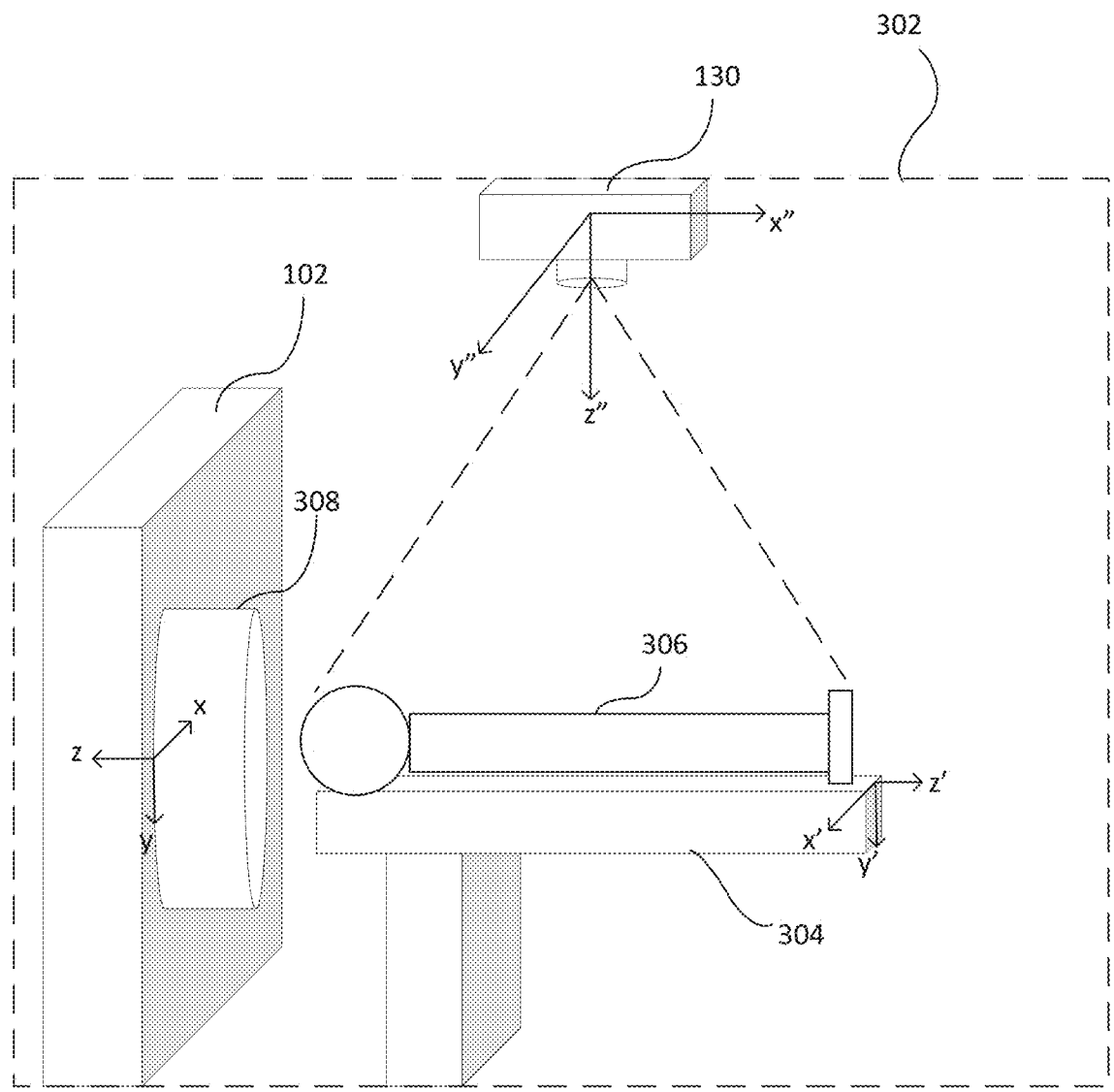
FIG. 3 illustrates an exemplary arrangement of a sensor.

FIG. 3 illustrates an exemplary arrangement of sensor 130. Sensor 130 is mounted on the ceiling 302 of a medical scanning room. Sensor 130 is located above the scan table 304 where a patient 306 may lie. As such, sensor 130 may acquire sensor data 132 of at least a portion or the whole body of the patient (or other objects of interest). Exemplary local coordinate systems (x, y, z), (x', y', z') and (x", y", z") for the gantry bore 308, the scan table 304 and sensor 130 respectively are also illustrated. Sensor 130 may also be mounted on an outer surface of the medical scanner 102 or inside the gantry bore 308 into which the patient is placed for scanning. In other implementations, sensor 130 is movably mounted on a rail (or other support elements) so as to allow motion following the object of interest and provide a better view of the object of interest.

Returning to FIG. 2, at 204, processing module 107 automatically interprets sensor data 132 to generate processing results. In some implementations, processing module 107 employs a machine learning algorithm to automatically interpret the sensor data. The machine learning algorithm may be based on, for instance, support vector machines, Bayesian classifiers, k-means clustering, decision trees, convolutional neural networks, deep belief networks, deep residual learning, reinforcement learning, recurrent neural networks, capsule networks, inductive programming, Siamese networks, generative adversarial networks, or a combination thereof. Other types of algorithms may also be used.

The processing results may include parameters (e.g., height, position) of objects of interest. Examples of such parameters include, but are not limited to, the height of the transfer bed and/or scan table, the size and/or shape of the patient, the weight of the patient, the position and pose of the patient on the scan table, the position of medical staff, the shape and position of equipment including equipment attached to the patient and/or the table (e.g., vital monitors, oxygen bottles, infusions, intravenous or IV lines) and/or other equipment (e.g., medical scanner, injector, trolleys), motion of equipment (e.g., cardiac compression device), image reconstruction parameters (e.g., orientation and extent of certain body regions of the patient), patient status, critical conditions of the patient (e.g., fear, pain, nausea, vomiting, allergic reaction, epilepsy), or a combination thereof.

At 206, control module 108 triggers one or more actions based on the processing results to support treatment of the patient. The one or more actions may be performed before, during and/or after medical scanning of the patient to support the scanning of the patient. Supporting the scanning of the patient includes, but is not limited to, setting the right scan table height to ease the patient transfer from the transfer bed, patient positioning for scanning, determining and preventing collisions, adapting volume of contrast agent to be administered to the patient, performing motion correction in image reconstruction, selecting image reconstruction field-of-view particularly for unusual poses, or a combination thereof. Other actions that may be performed to support treatment of the patient include, but are not limited to, responding to critical conditions of the patient, providing intervention support, assessing the patient, or a combination thereof. It should be appreciated that other actions may also be performed to support treatment of the patient.

More particularly, control module 108 may trigger one or more actions to facilitate patient positioning for scanning based on the processing results. For example, when the patient is brought into the medical scanning room on the transfer bed, processing module 107 may automatically identify the transfer bed and its height in previous step 204. Control module 108 may then automatically trigger an adjustment of the height of the scan table to align the upper surface of the scan table with the upper surface of the transfer bed in step 206. The scan table may be equipped with, for example, a motorized lift system that adjusts the height of the scan table in response to a signal triggered by control module 108.

The patient may also be positioned on the scan table prior to scanning. Different scanner types and scan modes pose different constraints on the patient position on the scan table. For example, only a certain z-axis range of the scan table can be used for the scanning, and the range for a flash mode CT scan is usually even shorter. Another example is dual-source CT that uses two separate x-ray tubes, one of which often provides a field-of-view that is smaller in the x- and y-dimensions. Accordingly, the patient must be properly placed on the table for different scanning technologies. Using the processing results (e.g., scan table height and dimensions, patient dimensions and body regions determined from sensor data) derived in previous step 204, along with the medical scanner constraints and geometry, control module 108 may determine the optimal position of the patient on the scan table. In some implementations, the optimal position may be presented (e.g., at workstation 103 or mobile device) as, for instance, an overlay of a live camera image of the patient on the scan table, so that the team can view it and move the patient to the optimal position. Alternatively, or in combination thereof, the relevant range may be projected directly on the scan table, so that it is visible while positioning the patient.

Based on the dimensions (e.g., length, body cross-section) of the patient detected from the sensor data 132, control module 108 may automatically determine the optimal height and horizontal movement range of the scan table for the medical scanning. For example, the optimal scan table height may be determined such that the isocenter of the body region to be examined is aligned with the isocenter of the medical scanner 102. This is important to obtain the best image quality-dose tradeoff in, for example, CT. If an imminent collision is detected, control module 108 may suggest a table height that is closest to the optimal table height which does not lead to a collision. A "collision" as used herein generally refers to a clash between objects, sometimes resulting in the pulling out of cables or devices. Control module 108 may also automatically determine the optimal horizontal examination range to cover the entire patient based on, for example, body landmarks (e.g., head top or feet) detected in the sensor data 132. If the examination is limited to a certain region (e.g. upper body), then the framework may limit the horizontal range accordingly based on body-region specific landmarks (e.g., shoulders, hips) detected in the sensor data 132. In some implementations, the scan table is not moved horizontally but the medical scanner 102 is moved instead. Control module 108 may set the horizontal movement range of the medical scanner 102 accordingly based on the sensor data 132.

In some implementations, control module 108 may determine and prevent imminent collision before and/or during scanning. Typically, polytrauma patients are connected to a lot of specialized medical equipment (e.g., vital signs monitors, oxygen bottles, infusion devices). Furthermore, accessories may be placed somewhere in the operating room (e.g., positioning/transfer aids). Before scanning, the team needs to ensure that the equipment is placed properly, such that collisions are not possible.

Using the processing results (e.g., positions of scan table and equipment) derived in previous step 204, along with the scanner setup parameters and selected protocol, control module 108 may determine the optimal position of the equipment to ensure a collision-free scanning. In some implementations, the optimal position may be presented (e.g., at workstation 103 or mobile device) as, for instance, an overlay of a live camera image of the equipment in the operating room, so that the team can view it and move the equipment to the optimal position.

Control module 108 may also compare the shape of the patient and equipment lying on the patient or scan table with the diameter of the gantry bore of the medical scanner 102. Control module 108 may then automatically determine a suitable scan table height to avoid collisions of the patient and/or equipment with the gantry. Some scanners 102 may be tilted in certain situations to obtain image data 120 that is skewed with respect to the length axis of the patient. In such cases, the collision detection needs to be performed with respect to an elliptical gantry bore instead of a cylindrical gantry bore. Based on the sensor data 132, control module 108 may automatically generate a suggestion to limit the tilt in order to avoid collisions. Besides scan preparation, control module 108 may detect any imminent collisions that may occur during scanning and trigger a warning (e.g., alarm or text message on workstation 103 or mobile device) to avoid such collisions. For imminent collision detection and prevention, two different workflows may be supported: (1) standard scanning (i.e., scan table moves) and (2) sliding-gantry setup (i.e., gantry moves). Collision detection and prevention may also be of interest for supporting the treatment of radiotherapy patients.

In other implementations, control module 108 may trigger one or more actions to respond to critical conditions of the patient based on the processing results. This may be performed continuously while the patient is present, and especially during scanning of the patient. Critical patient conditions include, for example, fear, panic, pain, nausea, vomiting, sweating, epilepsy, unconsciousness or leaking fluids (e.g., blood). Critical conditions need to be identified quickly for the team to respond rapidly.

Processing module 107 may automatically detect critical conditions in the previous step 204 based on sensor data 132 and especially camera images of, for example, the patient's facial expressions, body movements (e.g., respiratory depth or effort) and/or skin conditions. Other information that may be used by the processing module 107 to automatically detect critical conditions include, but are not limited to, heart rate, breathing rate and other sensor signal data (e.g., audio data to detect moaning). In the current step 206, control module 108 may then determine and trigger proper responses to detected critical conditions, which may range from generating an alert (e.g., alarm or warning message), providing calming voice commands to immediate termination of scanning. This is especially important when the patient is in the gantry and the team is outside of the operating room. Automatic critical condition detection is not only of interest for trauma patients, but also for other patient groups.

In some implementations, control module 108 may trigger one or more actions to adapt the volume of contrast agent to be administered based on the processing results. Contrast reduction is typically desired to reduce contrast load to the patient. However, sufficient contrast volume is required for adequate image quality to ensure proper assessment. Processing module 107 may automatically determine size and/or shape (e.g. tall-but-slim, apple-shaped, etc.) of patient in the previous step 204 based on one or more camera images of the patient. The shape of the patient's body may be necessary, since physiology not only depends on the weight of the patient that is derived from the size, but also on the distribution of body fat as indicated by the body shape. In the current step 206, control module 108 automatically calculates and adapts the optimal volume of administered contrast agent based on the scheduled examination and the determined patient size and/or shape. Weight-adapted contrast admittance is not only relevant for trauma patients, but for any patient requiring a contrast-enhanced scan.

In some implementations, control module 108 may trigger one or more actions to perform motion correction in image reconstruction. In some instances, to sustain blood circulation during scanning of hemodynamically unstable patients, some hospitals scan this patient group while the thorax of the patient is equipped with an automatic cardiac compression device (e.g., LUCAS® chest compression system). The regular compression of the chest results in a poor image reconstruction quality, as the thorax is highly affected by extreme motion artifacts.

Processing module 107 may automatically determine a motion model of the compression device in the previous step 204 based on sensor data 132. For example, a depth camera or a LIDAR sensor 130 may be used to track the elevation of the patient's chest over time. The motion introduced by the compression device may be accounted for by, for example, binning CT data from similar compression phases for reconstruction. In the current step 206, control module 108 automatically performs motion correction in image reconstruction using the motion model, resulting in motion-reduced medical images of the patient and, consequently, providing more diagnostic value.

In some implementations, control module 108 may trigger one or more actions to select an appropriate image reconstruction field-of-view particularly for unusual poses after scanning the patient. During image reconstruction, one of the most important quality aspects is to ensure that the field-of-view and orientation of the image reconstruction are correctly covering the required region of interest. This ensures that the images are standardized and easier for the radiologist to read. Normally, only a single topogram or scout image is acquired per body region (e.g., a lateral topogram for the head/neck area or an anterior/posterior topogram for the rest of the body). Based on this information, a skew of the body in the y/z or x/z plane, respectively, can be detected and accounted for. However, it is not possible to account for misalignments in all directions solely based on the topogram or scout, since these are only 2D projection images. Therefore, automatic field-of-view planning, which is necessary for a fully automatic reconstruction, can fail particularly for polytrauma patients, since they are typically lying in unusual poses (e.g., skewed/unaligned on the table). An example is a head scan image reconstruction: the image data of the head may be acquired with a lateral topogram. Using this information, z- and y-dimensions may be automatically identified. However, the third dimension (x-dimension) and the rotation cannot typically be identified automatically. To avoid corrupted image quality, radiographers typically perform a manual reconstruction planning, which is slower and results in a delayed diagnosis.

In the present framework, processing module 107 may automatically determine the true position and orientation of at least one region (e.g., head) of the patient on the scan table in the previous step 204 based on sensor data 132. For example, processing module 107 may detect body landmarks (e.g., head top, chin, ears, nose, and eye cavities) in camera depth images or in LIDAR measurements. This information may be augmented with landmarks detected in the topogram/scout image. Based on this information, processing module 107 may estimate the orientation of the head in all spatial directions. In the current step 206, control module 108 automatically determines the image reconstruction field-of-view (e.g., x-, y- and z-dimensions) and field orientation (e.g., rotations) based on the true position and orientation of the examination region. With the determined field-of-view and field orientation, a fully automatic image reconstruction may be performed without compromising on image quality with respect to field-of-view and orientation.

Figure 4A:
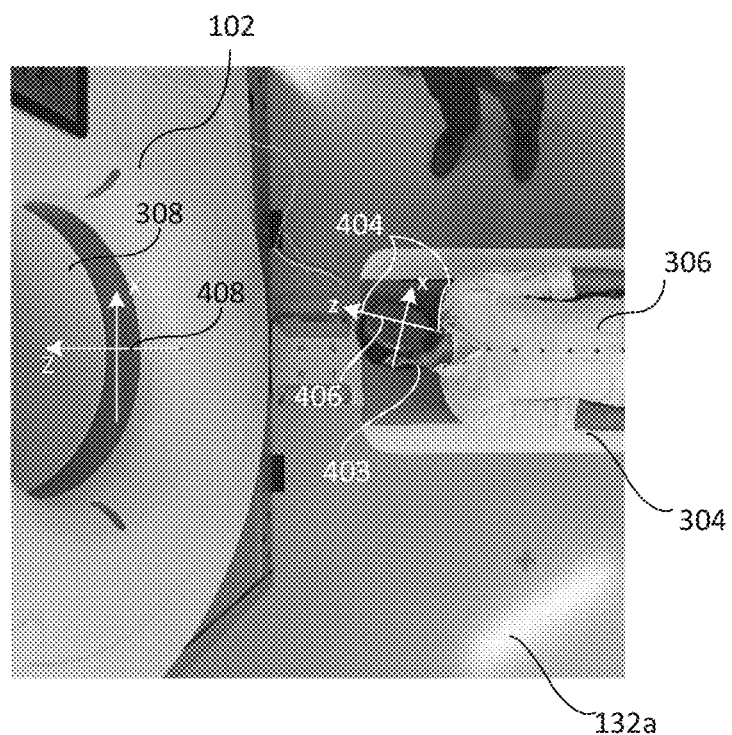
FIG. 4*a* shows an exemplary image acquired by a sensor showing a top view of a medical scanning arrangement.
Figure 4B:
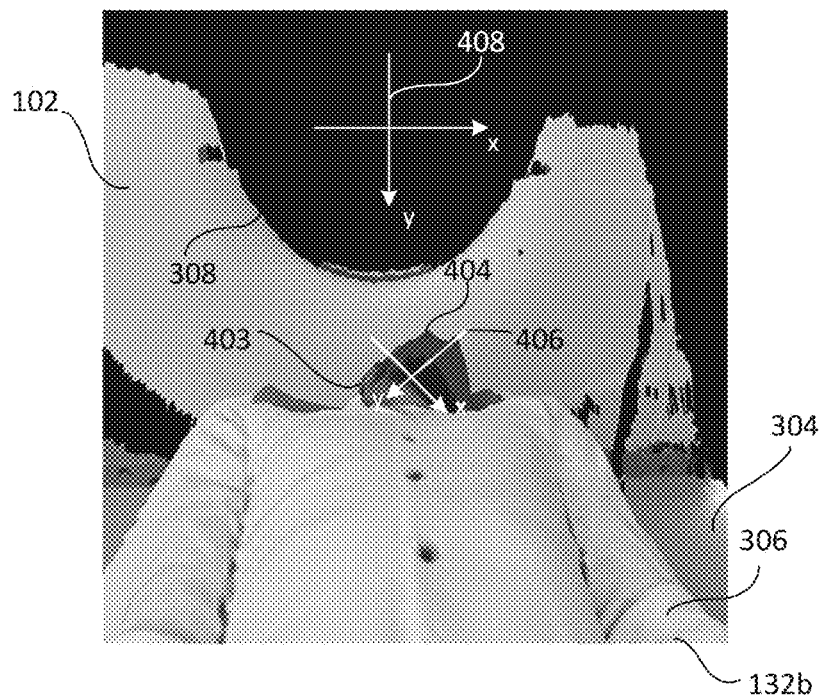
FIG. 4*b* shows another exemplary image acquired by a sensor showing another view of the medical scanning arrangement.

FIGS. 4a and 4b illustrate an exemplary correction of head misalignment. More particularly, FIG. 4a shows an exemplary image 132a acquired by sensor 130 showing a top view of a medical scanning arrangement. FIG. 4b shows another exemplary image 132b acquired by sensor 130 showing another view of the medical scanning arrangement. Images 132a and 132b may originate from the same sensor or they may be obtained from multiple sensors. A single acquisition by one sensor may be sufficient if the necessary structural information to determine the anatomical extents and orientation is captured.

The medical scanning arrangement includes a patient 306 lying on a scan table 304 in preparation for a scan by medical scanner 102. Sensor 130 may be, for example, a combined color image and depth camera mounted in the ceiling. Processing module 107 may determine the local patient frame-of-reference 406 of the patient's head 403 based on landmarks 404 detected in the sensor data 132a-b. The patient z-axis may be defined, for example, by the vector from the chin to the head. Together with a nose landmark, the y/z-plane may be defined. The x-axis may point from the visible right ear towards the invisible left ear. Although the left ear is invisible, the x-axis can be defined, because it is constrained to be perpendicular to the y/z-plane.

Additional anatomical landmarks (e.g., eye landmarks) that may be detected in the sensor data 132a-b may be used to further constrain the frame-of-reference 406 detection. The y-axis may be defined by the vector from the nose to the chin. Adding more constraints improves the robustness of the frame-of-reference extraction. Further approaches, such as learning the mapping through machine learning directly from the sensor data 132a-b without explicit landmark extraction may also be used. In the current step 206, control module 108 automatically aligns the patient-specific frame-of-reference 406 with the established medical coordinate system 408 to correct for head skew in the reconstructed medical data, allowing for standardized, more efficient reading of the images.

In some implementations, control module 108 may trigger one or more actions to provide intervention support after scanning. For the diagnosis of polytrauma patients, the radiologist typically goes to the scanner in order to perform a first diagnosis of life-threatening injuries directly there (e.g., at the patient, with the trauma team). Any identified injury is communicated to the trauma team. Certain injuries (e.g., tension pneumothorax, aortic rupture) may require an immediate intervention (e.g. puncture, balloon ablation) while the patient is still is on the scan table. The surgical/interventional expert takes the necessary anatomical information from the reading system and transfers it onto the patient.

To facilitate such intervention, the framework may automatically determine the presence of medical conditions like pneumothorax in the medical image data 120 acquired by medical scanner 102. Assuming the sensor 130 is calibrated to the medical scanner 102, processing module 107 may transform information about the location requiring intervention from the coordinate system of the medical image data into the coordinate system of the sensor 130. For example, if the sensor 130 is a combined color/depth camera, the recommended point for a puncture determined in the medical image data 120 can be indicated on a color image (or photograph) 132 of the patient, which may be presented to the interventional expert at, for example, an integrated display of the medical scanner 120 or workstation 103. The color image 132 may be augmented with further information obtained from the medical image data 120. For instance, risk structures (e.g., blood vessels, ribs) that should be avoided during the puncture can be overlaid on the color image 132. The expert performing the intervention is thereby relieved from the task of having to mentally transform the risk structures from the medical image data 120 to the outside of the patient. Instead, the information may be presented on a color image or photograph 132 of the patient, which resembles what the interventional expert actually sees. The sensor data (e.g., color image, photograph) 132 may be continuously updated. Once the interventional expert enters the field-of-view of the sensor 130 with the surgical instrument, the surgical instrument may be visually aligned to the planned intervention point while avoiding the risk structures. The overlays on the sensor data 132 may include, for example, the desired incision point, risk structure, location of injury, skeleton, vessel tree, area for further imaging, therapy, etc.

As an alternative to visualizing the information on a screen showing an image of the patient, in the current step 206, control module 108 may automatically trigger a projection of, for example, the determined region of interest directly onto the patient using, for example, a beamer or a laser projector, to guide the interventional expert. The sensor data 132 may also be used to register the patient in the frame of reference of different systems (e.g., CT, ultrasound, x-ray, C-arm, robots, etc.) such that all the systems are aware of the patient position and the region of interest on the patient.

In some implementations, control module 108 may trigger one or more actions to automatically assess the patient. This may be performed before, during or after scanning the patient. The automatic assessment may be performed according to established guidelines, such as the Advanced Trauma Life Support® (ATLS®) guidelines developed by the American College of Surgeons.

To facilitate such assessment, processing module 107 may automatically determine patient status in the previous step 204 based on sensor data 132 of the patient. Such patient status may include, but are not limited to, intubation and abnormal breathing patterns airways, changing patient face color in combination with increasing heart rate and decreasing blood pressure, leaking fluid (e.g., blood, urine), neurological disability (e.g., eye pupil movements and state of consciousness), overall body status or exposure (e.g., surface injuries, bruises, foreign bodies, burns, etc.). For example, a depth camera or a LIDAR sensor 130 may be used to track the elevation of the chest in order to detect abnormal breathing patterns. A color camera 130 may be used to acquire color images 132 for determining circulation issues indicated by changes of the facial color. Moreover, the movement of the eye pupils may be tracked in a color image stream to determine possible neurological disorders. Color images 132 may also be evaluated by algorithms to detect surface injuries, bruises, foreign bodies, burns, etc. This analysis may be complemented by, for instance, body surface temperature 132 measured by infrared sensors 130. In the current step 206, control module 108 automatically triggers a presentation of such patient conditions on workstation 103 and/or any other device (e.g., personal tablet, alarm) to alert the OR team to quickly respond.

Returning to FIG. 2, at 208, it is determined if the method 200 continues. The method may be determined to continue if, for example, the patient is detected to be still present in the operating room. If yes, the steps 202 through 206 are repeated to continue supporting treatment of the patient. If no, the method 200 ends.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. One or more non-transitory computer readable media embodying a program of instructions executable by machine to perform operations for patient treatment support, the operations comprising:
   acquiring, by one or more sensors, sensor data of one or more objects of interest;
   automatically interpreting the sensor data to generate processing results, including detecting one or more critical conditions of a patient based on one or more camera images of a facial expression, body movement, skin condition or a combination thereof of the patient; and
   triggering one or more actions based on the processing results to support treatment of a patient, including responding to the one or more critical conditions of the patient and supporting collision-free medical scanning of the patient by determining an optimal position of equipment based on the processing results in response to detecting an imminent collision with the equipment.

2. The one or more non-transitory computer readable media of claim 1 wherein the one or more objects of interest comprise at least a portion of the patient, a patient transfer bed, a scan table, medical equipment, medical staff, or a combination thereof.

3. The one or more non-transitory computer readable media of claim 1 wherein the processing results comprise a height of a transfer bed, a height of a scan table, a patient position, a patient size, a patient shape, a patient weight, positions of equipment, motion of equipment, image reconstruction parameters, a patient status, patient critical conditions, or a combination thereof.

4. The one or more non-transitory computer readable media of claim 1 wherein the supporting collision-free medical scanning of the patient comprises positioning the patient for scanning, adjusting a scan table height, determining and preventing collisions, adapting a volume of contrast agent to be administered to the patient, performing motion correction in an image reconstruction, selecting an image reconstruction field-of-view, or a combination thereof.

5. The one or more non-transitory computer readable media of claim 1 wherein the one or more actions further comprise providing intervention support.

6. A patient treatment support system comprising:
   one or more sensors that acquire sensor data of one or more objects of interest; and
   a computer system in communication with the one or more sensors, wherein the computer system includes
      a non-transitory memory device for storing computer readable program code, and
      a processor in communication with the non-transitory memory device, the processor being operative with the computer readable program code to perform operations including
         automatically interpreting the sensor data to generate processing results, including detecting one or more critical conditions of a patient based on one or more camera images of a facial expression, body movement, skin condition or a combination thereof of the patient, and
         triggering one or more actions based on the processing results to support treatment of a patient, including responding to the one or more critical conditions of the patient and supporting collision-free medical scanning of the patient by determining an optimal position of equipment based on the processing results in response to detecting an imminent collision with the equipment.

7. The system of claim 6 wherein the one or more sensors comprise a red-green-blue (RGB) camera, an infrared camera, a depth camera, a LIDAR sensor, a video camera, a plenoptic camera, a panoramic camera, a holographic camera, an ultrasound sensor, or a combination thereof.

8. The system of claim 6 wherein the one or more critical conditions comprise fear, panic, pain, nausea, vomiting, sweating, allergic reaction, epilepsy, unconsciousness, leaking fluid, or a combination thereof.

9. The system of claim 6 wherein the one or more sensors are mounted on a ceiling of a medical scanning room.

10. The system of claim 6 wherein the one or more sensors are mounted on an outer surface of a medical scanner.

11. The system of claim 6 wherein the one or more sensors are mounted inside a gantry bore of a medical scanner.

12. The system of claim 6 wherein the processor is operative with the computer readable program code to perform
interpreting the sensor data by determining a height of a transfer bed, and
supporting the collision-free medical scanning of the patient by triggering an adjustment of a height of a scan table based on the height of the transfer bed.

13. The system of claim 6 wherein the processor is operative with the computer readable program code to perform
interpreting the sensor data by determining a height and dimensions of a scan table, and dimensions of one or more body regions of the patient from the sensor data, and
supporting the collision-free medical scanning of the patient by determining an optimal position of the patient on the scan table based on the height and dimensions of the scan table, and the dimensions of the one or more body regions of the patient and medical scanner constraints.

14. The system of claim 6 wherein the processor is operative with the computer readable program code to perform
interpreting the sensor data by determining dimensions of the patient, and
supporting the collision-free medical scanning of the patient by determining an optimal height of a scan table based on the dimensions of the patient.

15. The system of claim 6 wherein the processor is operative with the computer readable program code to perform
interpreting the sensor data by detecting body landmarks on the patient, and
supporting the collision-free medical scanning of the patient by determining, based on the body landmarks, an optimal horizontal examination range to scan the patient.

16. The system of claim 6 wherein the processor is operative with the computer readable program code to perform
supporting the collision-free medical scanning of the patient by presenting the optimal position of the equipment on a live camera image of the equipment.

17. The system of claim 6 wherein the processor is operative with the computer readable program code to perform
responding to the one or more critical conditions of the patient by providing a calming voice command.

18. The system of claim 6 wherein the processor is operative with the computer readable program code to perform
interpreting the sensor data by determining a true position and orientation of at least one region of the patient on a scan table, and
supporting the collision-free medical scanning of the patient by determining an image reconstruction field-of-view and a field orientation based on the true position and the orientation.

19. The system of claim 6 wherein the processor is operative with the computer readable program code to perform
interpreting the sensor data by transforming information about a location requiring intervention from a first coordinate system of medical image data of the patient to a second coordinate system of the one or more sensors, and
triggering the one or more actions based on the processing results by indicating the location on the sensor data.

20. A method for supporting patient treatment, comprising:
acquiring, by one or more sensors, sensor data of one or more objects of interest;
automatically interpreting the sensor data to generate processing results, including detecting one or more critical conditions of a patient based on one or more camera images of a facial expression, body movement, skin condition or a combination thereof of the patient; and
triggering one or more actions based on the processing results to support treatment of a patient, including responding to the one or more critical conditions of the patient and supporting collision-free medical scanning of the patient by determining an optimal position of equipment based on the processing results in response to detecting an imminent collision with the equipment.

* * * * *